(12) United States Patent
Siebel et al.

(10) Patent No.: US 8,123,754 B2
(45) Date of Patent: Feb. 28, 2012

(54) SURGICAL JIG

(75) Inventors: Thomas Siebel, Puttlingen (DE); Tadgh O'Sullivan, Waterford (IE); Stuart Lindsey, Leeds (GB)

(73) Assignee: Depuy International Ltd. (GB)

( * ) Notice: Subject to any disclaimer, the term of this patent is extended or adjusted under 35 U.S.C. 154(b) by 882 days.

(21) Appl. No.: 11/569,523

(22) PCT Filed: Apr. 21, 2005

(86) PCT No.: PCT/GB2005/001528
§ 371 (c)(1),
(2), (4) Date: Nov. 6, 2007

(87) PCT Pub. No.: WO2005/112805
PCT Pub. Date: Dec. 1, 2005

(65) Prior Publication Data
US 2008/0183179 A1   Jul. 31, 2008

(30) Foreign Application Priority Data

May 22, 2004   (GB) .................................. 0411487.2

(51) Int. Cl.
*A61B 17/90* (2006.01)
(52) U.S. Cl. .......................................................... 606/89
(58) Field of Classification Search ................ 606/86 R, 606/87–89
See application file for complete search history.

(56) References Cited

U.S. PATENT DOCUMENTS

| | | | | |
|---|---|---|---|---|
| 4,896,663 A * | 1/1990 | Vandewalls | ...................... | 606/79 |
| 5,047,032 A * | 9/1991 | Jellicoe | ............................ | 606/83 |
| 5,312,409 A * | 5/1994 | McLaughlin et al. | ........... | 606/86 |
| 5,649,930 A * | 7/1997 | Dance et al. | ..................... | 606/88 |
| 5,690,638 A * | 11/1997 | Albrektsson et al. | ........... | 606/96 |
| 5,817,098 A * | 10/1998 | Albrektsson et al. | ........... | 606/96 |
| 6,520,969 B2 * | 2/2003 | Lambrecht et al. | ............ | 606/130 |
| 6,595,999 B2 * | 7/2003 | Marchione et al. | ............. | 606/96 |
| 6,928,742 B2 * | 8/2005 | Broers et al. | ..................... | 33/512 |
| 7,241,298 B2 * | 7/2007 | Nemec et al. | .................... | 606/86 |
| 7,488,325 B2 * | 2/2009 | Qian | ............................... | 606/96 |
| 7,488,329 B2 * | 2/2009 | Thelen et al. | ................... | 606/99 |
| 7,695,476 B2 * | 4/2010 | Nevelos et al. | ................. | 606/87 |
| 7,699,847 B2 * | 4/2010 | Sheldon et al. | ................. | 606/53 |
| 2002/0193801 A1 * | 12/2002 | Marchione et al. | ............. | 606/96 |
| 2005/0033290 A1 * | 2/2005 | Nevelos et al. | ................. | 606/53 |
| 2005/0245936 A1 * | 11/2005 | Tuke et al. | ...................... | 606/89 |

FOREIGN PATENT DOCUMENTS

| | | |
|---|---|---|
| DE | 1164019 B | 2/1964 |
| DE | 10322760 A1 | 12/2004 |
| EP | 1477120 A | 11/2004 |
| EP | 1477120 A1 | 11/2004 |
| FR | 2294685 A | 7/1976 |
| FR | 2294685 A1 | 7/1976 |
| WO | 2005/112805 A2 | 12/2005 |
| WO | WO 2005112805 A2 | 12/2005 |

OTHER PUBLICATIONS

Siebel, T; German Patent No. DE10322760A1; Dec. 2, 2004; English Abstract; Derwent World Patents Index;© 2009 Derwent Information Ltd. ; Dialog® File No. 351 Accession No. 14653173.

(Continued)

*Primary Examiner* — Thomas C. Barrett
*Assistant Examiner* — Christopher Beccia

(57) ABSTRACT

A surgical jig and method of use in image guided and non-guided surgery are described. The jig is for use in determining an axis of a body part. The jig includes a handle at a proximal end and a mouth at a distal end. The mouth is engagable about the body part and defines a substantially flat plane. A guide has a channel with an axis substantially perpendicular to the plane and a support attaches the guide to the jig. The guide can be translatable relative to the mouth while maintaining the axis substantially perpendicular to the plane. The method determines an axis relative to a body part using the jig. The method comprises engaging the mouth about the body part and translating the guide relative to the mouth so as to align the axis of the channel with the axis of the body part.

26 Claims, 10 Drawing Sheets

OTHER PUBLICATIONS

Tornier, R: French Patent No. FR2294685AI Aug. 20, 1976; English Abstract; Derwent World Patents Index;© 2009 Derwent Information Ltd. ; Dialog® File No. 351 Accession No. 1228166.

PCT International Search Report PCT/GB2005/001528 dated Dec. 6, 2005 pp. 4-5.

PCT Written Opinion, 8 pages.

International Search Report, 6 pages.

PCT Request, 4 pages.

* cited by examiner

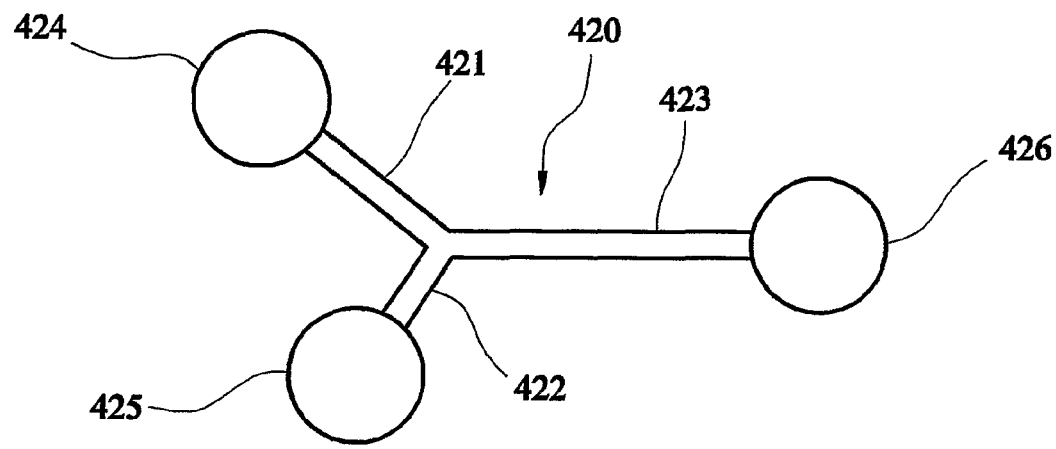
FIG. 7
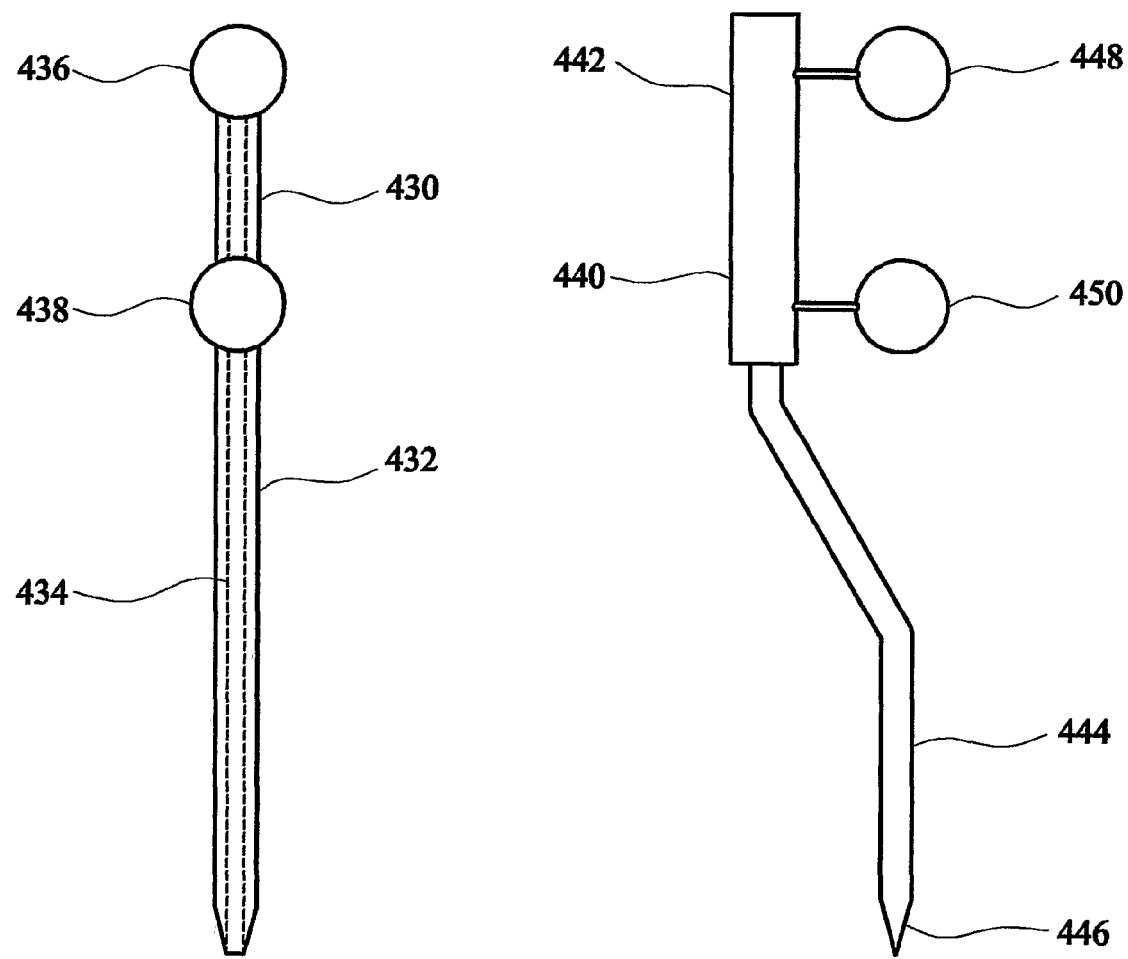
FIG. 8A
FIG. 8B

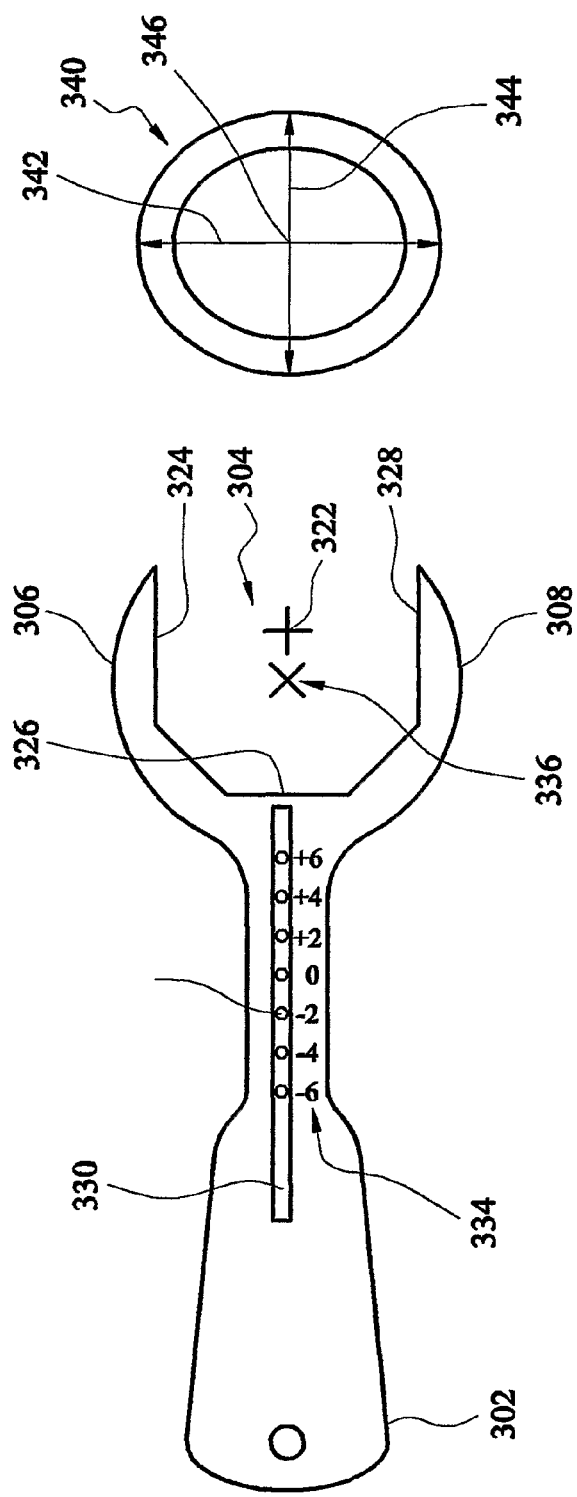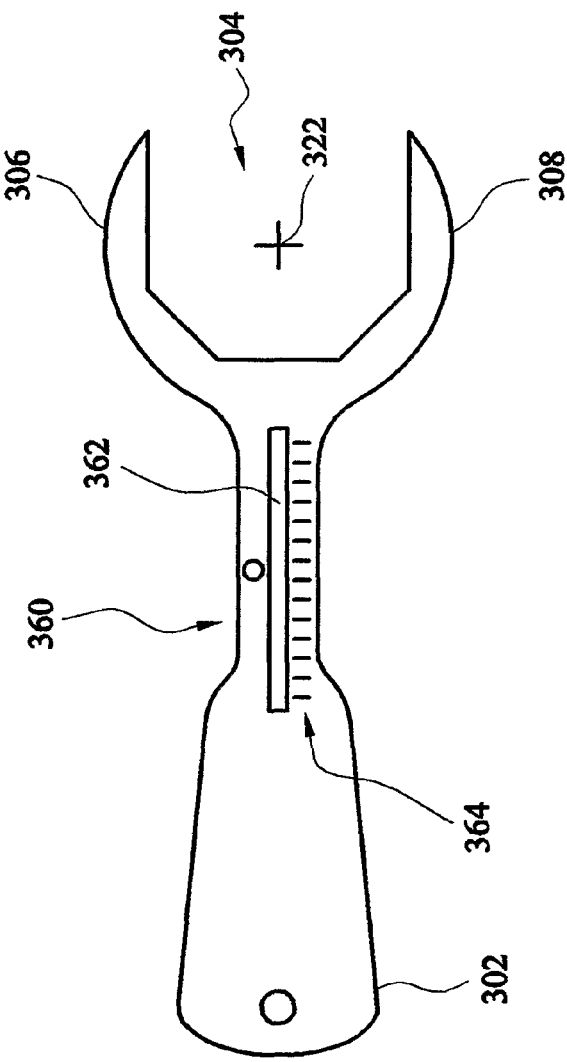
FIG. 10A
FIG. 10B

SURGICAL JIG

The present invention relates to a jig, and in particular to a surgical jig for use in determining an axis of a body part.

In many surgical procedures and operations it can be necessary to determine an axis of a body part having a complex, often non-uniform, geometry. This can be achieved by the surgeon "eye-balling", i.e. visually assessing, the body part to determine where, and at what angle, to start drilling, cutting or carrying out any other invasive surgical procedure. This approach is limited in its accuracy and its successful utilisation can be highly dependent on the skill and experience of the surgeon. The results of a badly carried out procedure can be exacerbated in surgical procedures in which a correct determination of the axis position is important in order to ensure the correct mechanical functioning of the body part in the overall mechanical functioning of the body.

For example in the area of implants, if an axis is incorrectly determined intra-operatively, then the implant can be incorrectly positioned which can give rise to various difficulties such as incorrect patient limb motion, pain, incorrect mechanical functioning of the implant, excessive wear of the implant and further damage to the body part. Therefore it would be desirable to be able to provide a device for assisting in the accurate determination of an axis of a body part. It would be further advantageous if the device could be used with a reduced amount of trauma to soft tissues surrounding the body part.

According to a first aspect of the invention, there is provided a surgical jig for use in determining an axis relative to a body part. The jig can include a handle at a proximal end and a mouth at a distal end. The mouth can be engagable about the body part and can define a substantially flat plane. A guide has a channel with a guide axis substantially perpendicular to the plane. A support attaches the guide to the jig. The guide can be translatable relative to the mouth with the guide axis substantially perpendicular to the plane.

The jig can be used for determining the anatomical axis of the body part itself, an axis or linear direction of the body part, or for determining any axis or linear direction relative to the body part received in its mouth. All of the foregoing are considered to fall within "axis relative to a body part". By providing an open mouth into which a body part is received, the amount of trauma experienced by soft tissues about the body part is reduced. Also, the mouth helps to coarsely align the jig with the body part axis. The translatable guide provides fine tuning of the guide axis in cases where body part morphology or other constraints require.

The mouth can include formations adapted to mate with an anatomical feature or features of the body part. By providing the mouth with a shape corresponding to the outer surface or parts of the outer surface of the body part, this helps to provide an auto-locating feature which facilitates the correct initial positioning of the jig and also allows a surgeon to use feel to determine whether the jig has been correctly positioned. The formations can be adapted to engage with any anatomical formations that are characteristic of the body part. The formations can comprise a first concave formation and a second concave formation. The formations can be located on opposite sides of the mouth. The formations can be oriented in opposite directions to each other. The formations can be adapted to engage parts of a femoral neck on opposed sides of the femoral neck.

The channel can be a closed bore or an at least partially open channel provided the channel can function to retain an instrument aligned with the guide axis in use. The channel can have a curved, elliptical, oval, regular or irregular rectilinear cross section. The channel preferably has a circular cross section.

The support can provide a sight. The support can have a transverse dimension substantially less than its longitudinal dimension, such that the support can provide sight in use by a surgeon to help align the jig with the body part using visual landmarks at the surgical sight during positioning and manipulation of the jig.

The support can be constrained to translate along a central or middle longitudinal axis of the jig. The support can be slidably mounted on the jig. The support can be slidably mounted to a body part of the jig, between the handles and mouth. The support can comprise an arm. The arm can have a first free end and a second end. The guide can be attached at the free end and the support can be mounted to the jig by the second end.

The jig can includes a forceps part. The forceps part can provide the mouth and the handle. The jig can include a drive mechanism operable to open and/or close the mouth. The jig can also include a lock operable to lock the mouth in an open or closed position. The lock can be provided as a part of the drive mechanism.

The support can include or be attached to a base at the second end of the arm. The base can be constrained to slide along a middle axis of the jig. When the jig includes a forceps part, the forceps can include a pivot. A part of the pivot can serve to retain the base against the forceps part. The forceps can also include a retaining formation located equidistant between arm parts of the handle of the forceps. The retaining formation can be configured to remain equidistant between arm parts of the handle of the forceps as the arm parts are opened and closed. The base can co-operate with a part of the pivot and the retaining formation to be constrained to slide along the middle axis. In this way the guide axis is maintained at a position along the middle of the mouth as it is translated along the middle axis.

The drive mechanism can include a threaded boss located on each arm part of the handle of the forceps, a threaded shaft extending between the bosses, the shaft having opposite sense screw threads on either end, and a manually or powered drive member mounted on the centre of the threaded shaft, wherein rotation of the shaft in a first direction opens the mouth and rotation of the shaft in a second direction closes the mouth. The drive member can be a wheel. The screw threads on the shaft can be single, multi-start, 2-start or 3-start threads. Multi-start threads provide a significant mechanical advantage in providing a large degree of opening or closing of the forceps for a small degree of rotation of the shaft. This improves the ease of use of the jig by a surgeon in practice.

The drive member can provides the retaining formation. The retaining formation can engage with a slot or channel part of the support. The parts of the support defining the slot or channel can pass below the a part of the drive mechanism to help retain the support against the forceps. The drive member can be in the form of wheel. The wheel can bear formations providing a grip.

The jig can include a marker detectable by an image guided surgery (IGS) system. Hence the location of the jig, including its position and orientation in space, can be determined by the IGS system. The marker can be stationary relative to the guide axis. Hence, the location of the guide axis is correlated with the position of the marker. The marker can be provided as a part of the support or support assembly. The marker can be permanently or releasably attached to the jig.

The marker can detectable by a wire based or a wireless IGS system. The marker can provide a source of radiation.

The marker can reflect or otherwise transmit radiation. The radiation can be electromagnetic or sonic. The radiation can be in the visible, infrared, radio or microwave parts of the electromagnetic spectrum.

The jig can further comprise an instrument with at least a straight portion within the channel and extending at least partially along the guide axis. Hence at least a part of the instrument can be aligned with the body part determined by the guide axis of the guide. The instrument can be cannulated. In this way the bore of the cannular can aligned with the axis of the body part using the jig. The instrument can be a drill guide. The instrument can provide a bushing for supporting a drill bit used to drill a hole along the body part axis determined by the jig. The instrument can be movable along the guide axis. The instrument can include a formation which can co-operate with a part of the guide to lock the instrument in position at a position along the guide axis.

The instrument can be resiliently biased toward the mouth. The instrument and guide can between them provide a spring which interacts between the guide and instrument to urge the instrument toward the mouth. In this way, the jig can be self-locking about the body part, without requiring further adjustment of the instrument part.

The instrument and the guide can provide between them an external thread and an internal thread. The threads between them provide a mechanism for adjusting the travel of the instrument along the guide axis and also for locking the jig to the body part.

The instrument can includes a portion having a smooth outer surface and a right circular cylindrical shape. This portion of the instrument can provide an axle about which a part of a checking stylus can be journaled for rotation about the guide axis. This allows a check for neck-notching to be carried out with the jig in situ.

The instrument can include a marker detectable by an image guided surgery system to locate the instrument and/or guide axis. The marker can be similar to those mentioned above in relation to the jig.

According to a further aspect of the invention, there is provided a kit of parts for use in determining an axis of a body part, the kit comprising a jig according to the preceding aspect of the invention, and an instrument. The instrument can be adapted to be located within the channel and to be translatable along the guide axis. The instrument can have any of the features mentioned above.

The kit can further comprise a marker detectable by an image guided surgery system. The marker can be attached or attachable to the jig or instrument, to allow the guide axis to be located by an IGS system.

According to a further aspect of the invention, there is provided a jig for use in determining an axis of the femoral neck. The jig can comprise a forceps part including a mouth and a pair of handles, the mouth being engagable about the femoral neck. The mouth can define a substantially flat plane. The mouth can include opposed jaws each bearing concave formations adapted to engage anatomical parts of the femoral neck. The jig can include a support comprising a base and an arm. The base can be slidably attached to the forceps part and the arm can extend from the base and away from the plane of the mouth. The arm can further have a holder with a cylindrical channel therein at a free end of the arm. The channel can have a longitudinal axis extending in a direction substantially perpendicular to the plane of the mouth. A cannulated drill guide can be received within the channel and be movable along the axis.

In use the drill guide can be brought into contact with the femoral head to clamp the jig about the femoral head. This provides a guide for drilling a hole along the axis of the femoral neck. The hole can be for receiving a part of an implant or surgical instrument.

According to a further aspect of the invention, there is provided a method for determining an axis relative to a body part using a jig having a handle, a mouth defining a substantially flat plane, and a guide having a channel with a guide axis substantially perpendicular to the plane. The method can comprise engaging the mouth about a body part. The guide can be translated relative to the mouth so as to align the guide axis of the channel with the axis of the body part.

An instrument can be located in the guide and moved along the guide axis to clamp the jig about the body part. A tool or instrument can be inserted into the guide or into an instrument in the guide to carry out further surgical steps.

According to a further aspect of the invention, there is provided a method for determining an axis relative to a body part using a jig having a handle, a mouth defining a substantially flat plane, a guide having a channel with a guide axis substantially perpendicular to the plane and a marker detectable by an image guided surgery system. The method can comprise engaging the mouth about a body part. The marker cab be detected and the location in space of the axis of the channel can be determined. A visual representation of the axis of the channel and/or a visual representation of the axis of the body part can be provided. The guide can be translated relative to the mouth to more closely align the visual representations of the guide axis and body axis. The visual representations of the axis of the body and guide axis can be brought substantially co-linear.

According to a further aspect of the invention, there is provided a surgical jig for use in determining an axis relative to a body part. The jig can include a handle, a mouth engagable about the body part and defining a substantially flat plane, a guide having a channel with a guide axis substantially perpendicular to the plane and a support. the support can attach or fasten the guide to the jig at a plurality of positions on the jig, so that at any of the positions the guide is substantially perpendicular to the plane.

The plurality of positions can have a discrete range or continuous range of values.

The jig can include a scale indicating the off-set from a centre of circular symmetry of the mouth of the jig for the position of attachment of the support arm to the jig. The offset can be along the longitudinal axis of the jig.

According to a further aspect of the invention, there is provided a method for determining an axis relative to a body part using a jig, comprising determining a first dimension of the body part, determining a second dimension of the body part and fastening a guide part of a jig to a body part of a jig at a position which compensates for deviations from a circular symmetric cross sectional shape of the body part. The guide axis can be provided substantially perpendicularly to the plane of a mouth of the jig.

With respect to method aspects of the invention, the jig can be used in any surgical procedure in which it is desired to determine an axis or linear direction in relation to a body part to which the jig is attached. The jig is particularly suitable for use with a femoral neck and head and in particular as part of a femoral head resurfacing operation.

An embodiment of the invention will now be described, by way of example only, and with reference to the accompanying drawings, in which:

FIG. 7 shows a schematic illustration of an image guided surgery marker part of an image guided surgery adapted version of the surgical jigs shown in FIGS. 1 to 5;

FIGS. 8A and 8B show schematic illustrations of first and second image guided surgery instruments for use with the surgical jigs shown in FIGS. 1 to 5;

FIGS. 10A and 10B show schematic plan views of further embodiments of a body part of the jig according to the invention.

Figure 1:
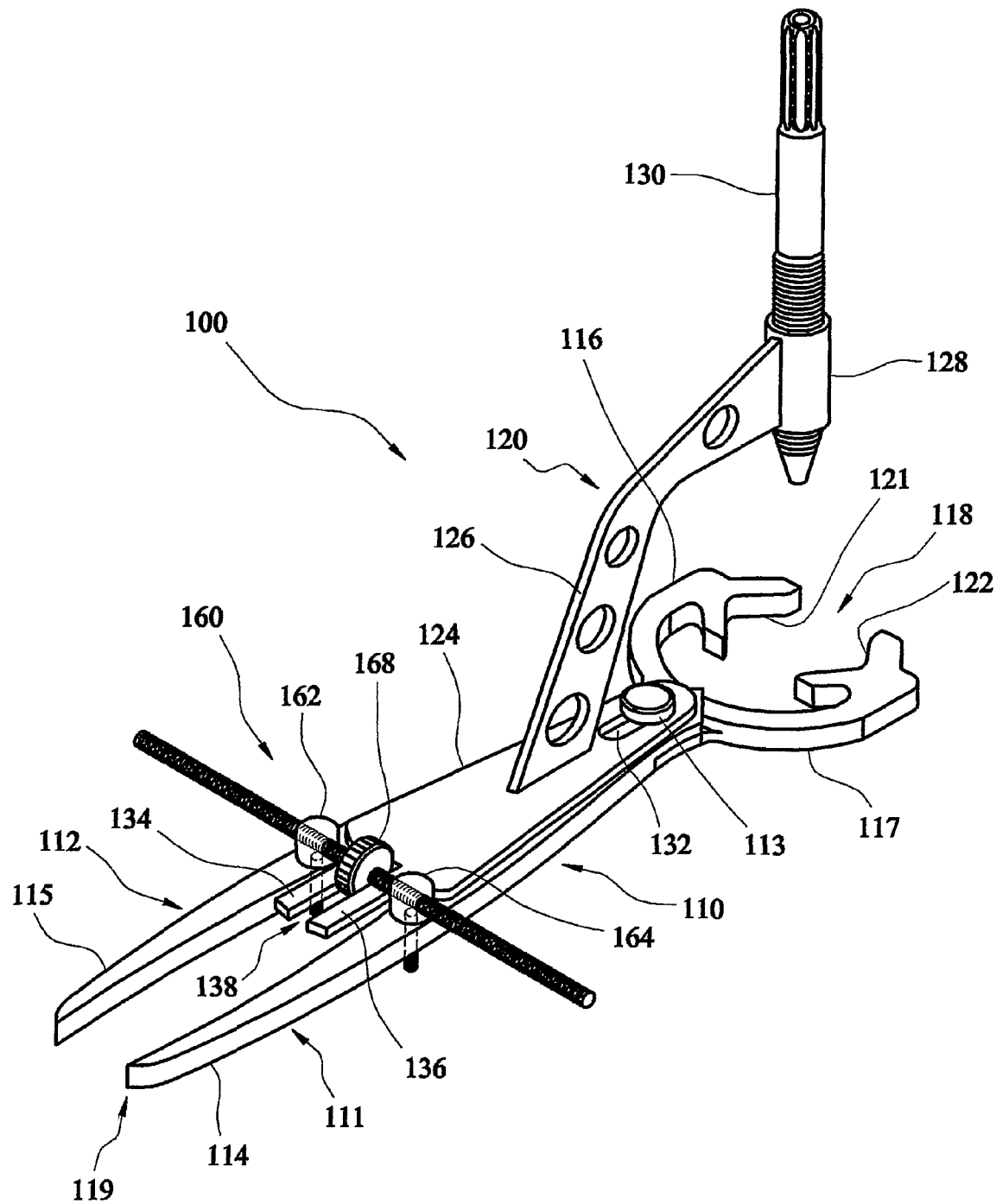
FIG. 1 shows a perspective view of a first surgical jig according to the present invention.

Similar items in different Figures share common reference numerals unless indicated otherwise. Some features of the drawings are shown in ghost lines to indicate that they are normally hidden from view.

Various embodiments of the invention will now be described in greater detail with specific reference to their use in relation to a femoral body part in hip surgery and in particular a femoral head resurfacing part of that surgical procedure. However, the invention is not limited to use in that particular surgical procedure, nor is its use limited to the femur. Rather, the invention can be utilised in connection with any bone or body part for which it is desired to identify a particular axis of that body part and as part of any surgical procedure whether involving implants or not.

Figure 2:
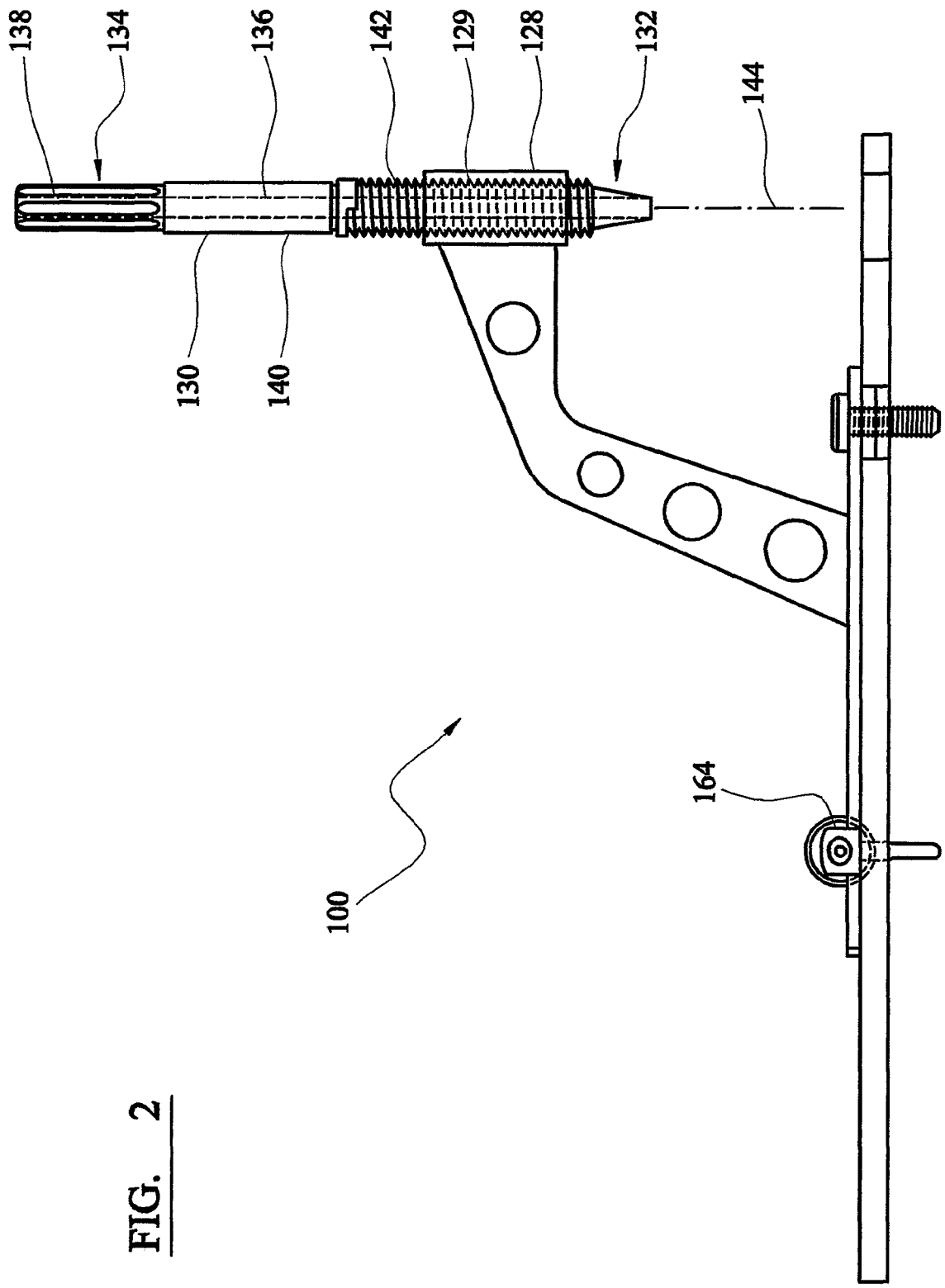
FIG. 2 shows a side elevation of the surgical jig shown in FIG. 1.
Figure 3:
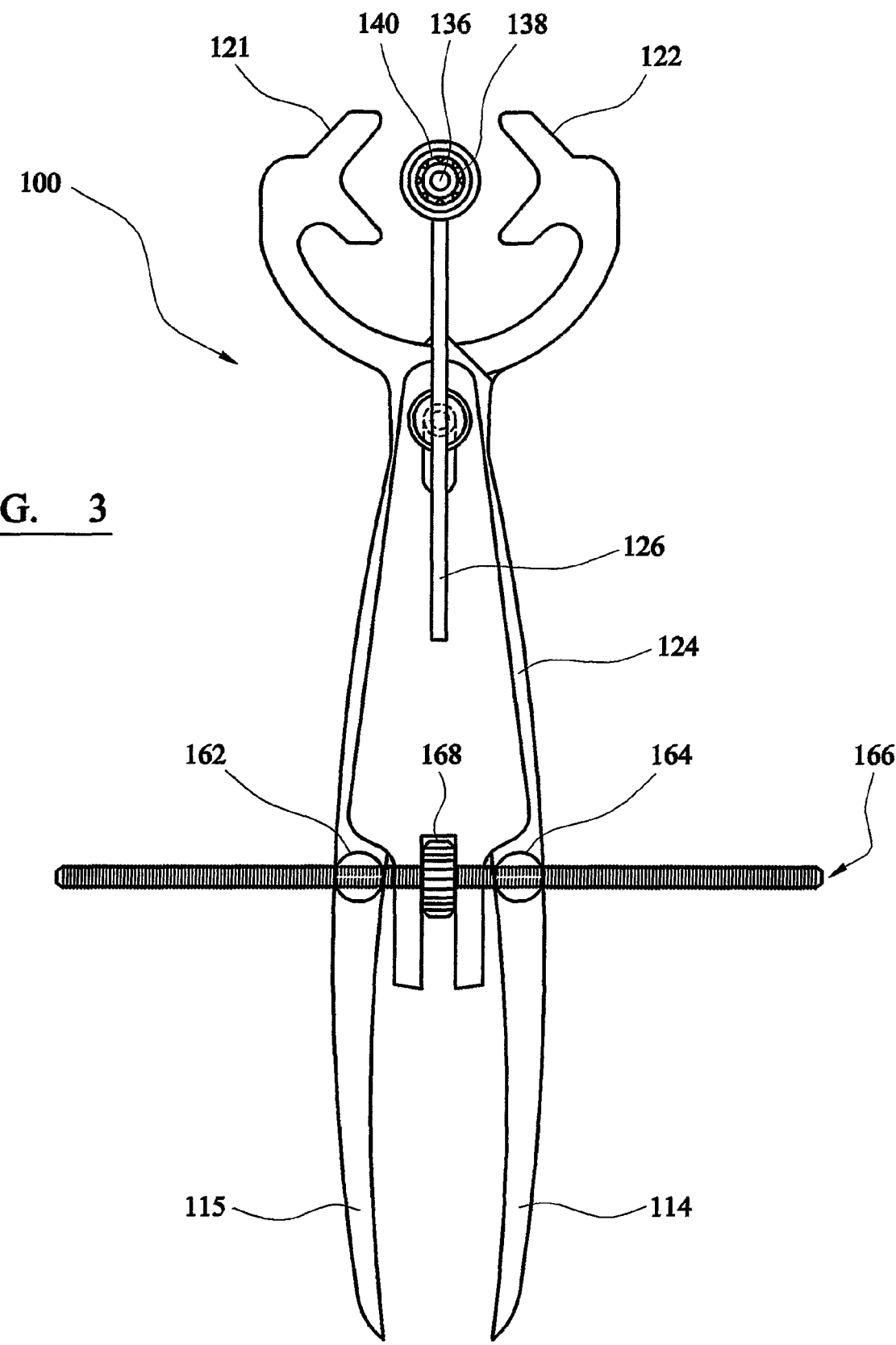
FIG. 3 shows a plan elevation of the surgical jig shown in FIG. 1.

With reference to FIGS. 1 to 3, there is shown a first surgical jig 100 according to the present invention. The jig includes a forceps part 110 on which a support assembly 120 is mounted. The forceps part 110 comprises a first element 111 and second element 112 pivotally connected by a threaded screw 113 passing through commonly aligned respective apertures in elements 111 and 112. Element 111 has an extended elongate portion providing a first arm 114 and similarly element 112 has an extended elongate portion providing arm 115. Between them arms 115 and 114 provide a handle 119 toward a proximal end of jig 100.

Element 111 also has a curved part 116 providing a first jaw of the forceps. Similarly, element 112 has a substantially mirror image curved part 117 providing a second jaw. Between them, jaws 117 and 116 define an open mouth 118 toward a distal end of the jig. The mouth lies in and defines a substantially flat plane. A generally concave formation 121, 122 is provided at the free end of each of jaws 116 and 117. The concave formations are adapted to engage with an anatomical body part in use, as will be described in greater detail below.

Support 120 includes a base 124 having an arm 126 extending therefrom. A guide 128 is attached to the free end of arm 126 and an instrument 130 is located within guide 128.

Base 124 is a substantially flat planar member and has a linear slot 132 therein toward a first end. Screw 113 passes through slot 132 and the head of screw 113 retains base 124 against the forceps. A first member 134 and a second member 136 extend from a second end of base 124 defining a channel 138 there between. Channel 138 retains a wheel 168 of a drive mechanism 160 which will be described in greater detail below. Base 124 can slide relative to forceps 110 and the motion of support 120 is constrained to be in a straight line along the middle or central axis of the forceps by the cooperation of the wheel 168 of the drive mechanism in channel 138 and the screw 113 in slot 132. Hence, support 120 is constrained to translate lineally along the middle axis of the jig.

Arm 126 is thin, i.e. its dimension in its lateral direction is significantly smaller than its dimension in its longitudinal direction. In this way, the arm provides a sight in use to facilitate alignment of the jig relative to a body part. Arm 126 has a plurality of apertures therein, four in the embodiment shown, and these help reduce the weight of the arm and also allow the surgeon to look through the arm to enhance the surgeon's view of the surgical sight.

Guide 128 is in the form of a right circular cylinder having a right circular cylindrical channel there through. The guide is located such that the centre of the channel lies on the middle longitudinal axis of the guide and with the longitudinal central axis of the channel substantially perpendicular to the plane defined by the mouth of the forceps. An inner surface of guide 128 has a screw thread therein which cooperates with an external thread on instrument 130 as will be described in greater detail below. Although shown as a closed cylinder, in another embodiment, guide 128 could have a partially open structure, such as a C shape in cross section. Indeed any geometry of guide which can retain an instrument could be used.

Instrument 130, in this embodiment, provides a drill guide. The drill guide has a generally elongate, straight form and includes a head part 132 and a tail part 134. Instrument 130 is cannulated and includes a bore 136 extending along its length. Tail 134 includes a plurality of raised ribs extending in a longitudinal direction and which provide an engagement for a tool to rotate the instrument about its longitudinal axis in use. An intermediate portion 140 of instrument 130 has a smooth right circular cylindrical outer surface. This part of the instrument provides a shaft around which a stylus can be rotated during a procedure for checking for neck notching as will be described in greater detail below.

An externally threaded portion 142 is also provided which corporates with thread 129 in guide 128 so that the instrument can be screwed into or out of the guide so as to translate the instrument along the central axis of the guide 144. Although cooperating threads are used as a mechanism to allow the instrument to be progressed along the guide axis 144, other mechanisms can be used. For example, a resilient biasing means, such as a spring, can be used to urge the instrument toward the forceps head with the instrument having a smooth outer surface running inside a smooth inner surface of guide 128.

Drive mechanism 160 includes a first boss 162 mounted on forceps arm 115 and a second boss 164 mounted on forceps arm 114. Each boss is mounted by a threaded element extending through a cooperating threaded aperture in each forceps arm. Each boss has a threaded aperture extending there it and along an axis substantially transverse to the longitudinal axis of the forceps. A threaded bar 166 has a wheel 168 mounted thereon at the middle of the bar and on the central axis of the forceps. The threads on either end of the bar have opposite senses and can be multi-start threads. Wheel 168 has raised rib formations thereon providing a grip. In a preferred embodiment, the bar has three start threads although in other embodiments, two start and single threads can also be used. A multi-start thread provides large relative degrees of motion of the arms of the forceps as a result of a small rotation of the wheel.

The drive mechanism includes a lock so that the forceps can be locked in a preferred configuration. For example, the lock can be provided by a plastics coating on the thread of the bushes. In another embodiment a nylon collar can be provided external to and adjacent a side of the bushes, and through which the threaded rod passes, such that friction prevents the thread from undoing. In use, when wheel 168 is rotated in a first direction, the rotating rod acts on the threads in bushes 162 and 164 and drives the handles 115, 114 of the forceps apart thereby opening jaws 116 and 117. Rotating wheel 168 in the opposite direction draws the handles 115 and 114 together thereby closing jaws 116 and 117. Wheel 168 is located along the central longitudinal axis of the forceps and, as the pitches of the threads on the rod 166 are the same, the wheel 168 stays positioned on the central axis as the arms are opened or closed. As wheel 168 and screw 113 both lie on the middle axis of the forceps, base plate 124 is also maintained centrally when the forceps are opened and closed and can slide backwards and forwards along the central axis of the forceps.

All the major components of the jig are made from surgical stainless steel, although other bio-compatible materials can be used, such as plastics.

Figure 4A:
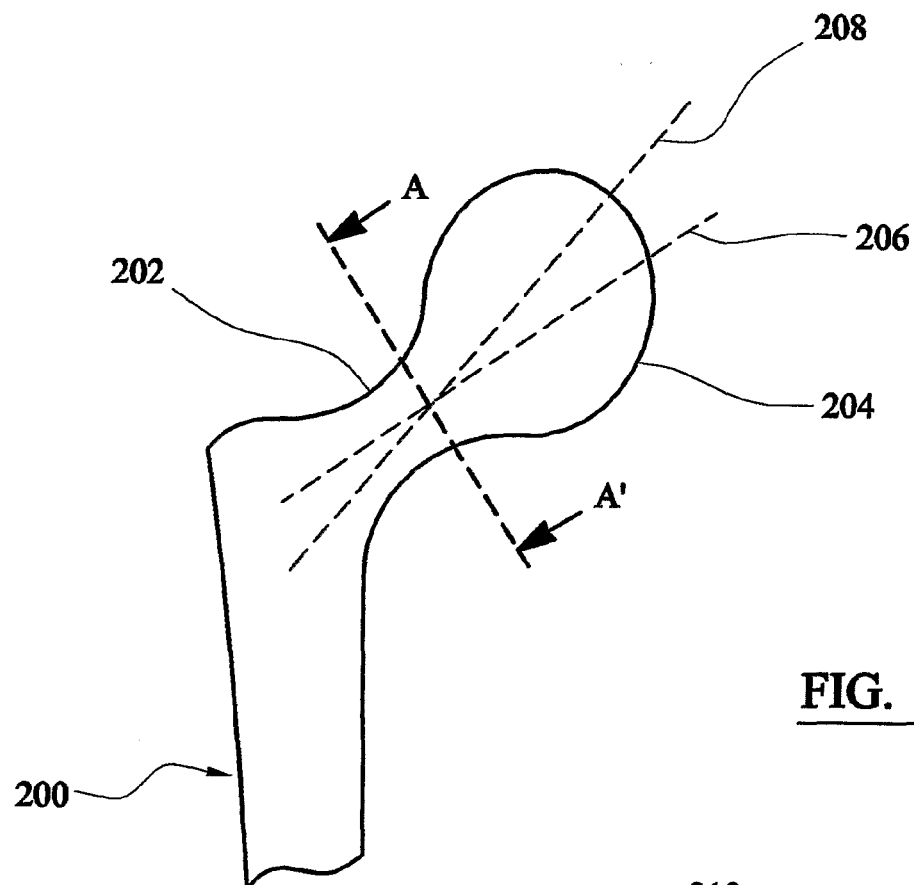
FIG. 4A shows a schematic illustration of a top part of a femur.

The function of the jig will now be further explained with reference to FIGS. 4A and 4B. FIG. 4A shows a top part of a femur 200 including a femoral neck 202 and femoral head 204. The femoral neck 202 constitutes a body part having an axis 206 which it is desired to determine. The axis 206 may coincide with an anatomical axis or may merely be a specific direction required as part of a surgical procedure, e.g. along which to drill a hole. From a visual inspection of head 204, it may appear that the axis of the body part is axis 208, but as can be seen, axis 208 differs from the actual axis 206 of the neck 202. There is variation in the exact geometry of the femoral head and neck and therefore it can be difficult in practice to reliably identify the axis of the neck 206 in order to ensure that an implant is correctly positioned. The jig of the present invention helps to ensure that the axis of the body part is more accurately and easily determined, or a suitably close approximation to its location is determined.

Figure 4B:
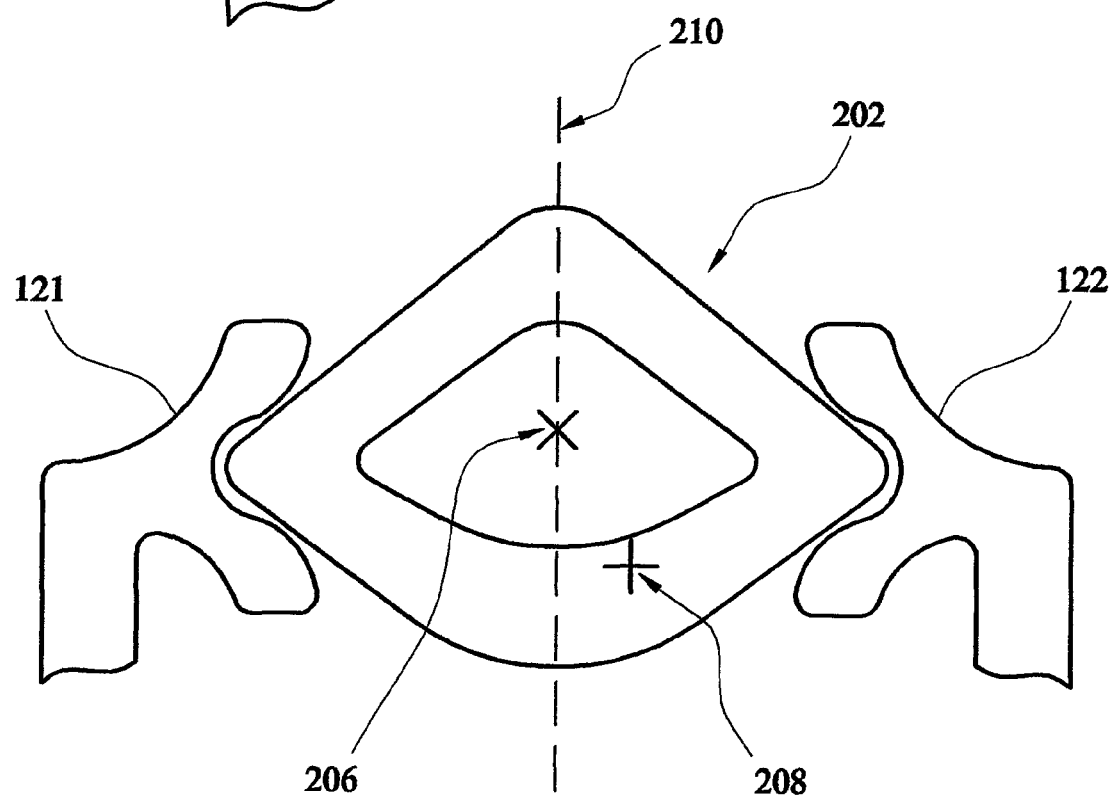
FIG. 4B shows a schematic illustration of a cross section through a femoral neck.

FIG. 4B shows a schematic cross section through the femoral neck along line AA' of FIG. 4A and illustrate engagement of the jaws of the forceps about the femoral neck 202. As illustrated in FIG. 4B, the forceps have been brought into engagement about the femoral neck from a lateral to medium direction. As the jig has an open mouth, the jig does not disturb soft tissue to the medial side of the femoral neck. Hence the open mouth of the jig helps to reduce trauma to soft tissues and can make the surgical procedure more simple. The concave formations 121 and 122 are shaped to engage with anatomical features on the sides of the femoral neck so as to reliably locate the jig with respect to the neck.

It has been found that the anatomical axis of the neck generally falls midway between the sides gripped by the forceps. Hence by gripping about the neck, the jig helps to automatically locate, to a useful degree of reliability, the middle line of the femoral neck on, or close to which, the axis 206 tends to lie. The anatomical axis that might be identified from a visual inspection alone of the femoral head 204, e.g. axis 208, as can be seen, falls away from the position of the axis of the femoral neck 206 as illustrated in FIG. 4B. As the femoral neck is not necessarily symmetric in the medial to lateral direction, it has been found to be beneficial to provide a degree of freedom of movement along line 210 which is substantially midway between the jaws of the forceps and therefore lies on the central line of the forceps. Hence, in order to fine tune the location of the femoral neck axis 206, the surgeon can use visual cues from the surgical site to translate the support backward and forward along line 210 so as to more accurately determine the body part axis by the position of the central longitudinal axis of guide 128, and taking into account variations in body part morphology.

Figure 5:
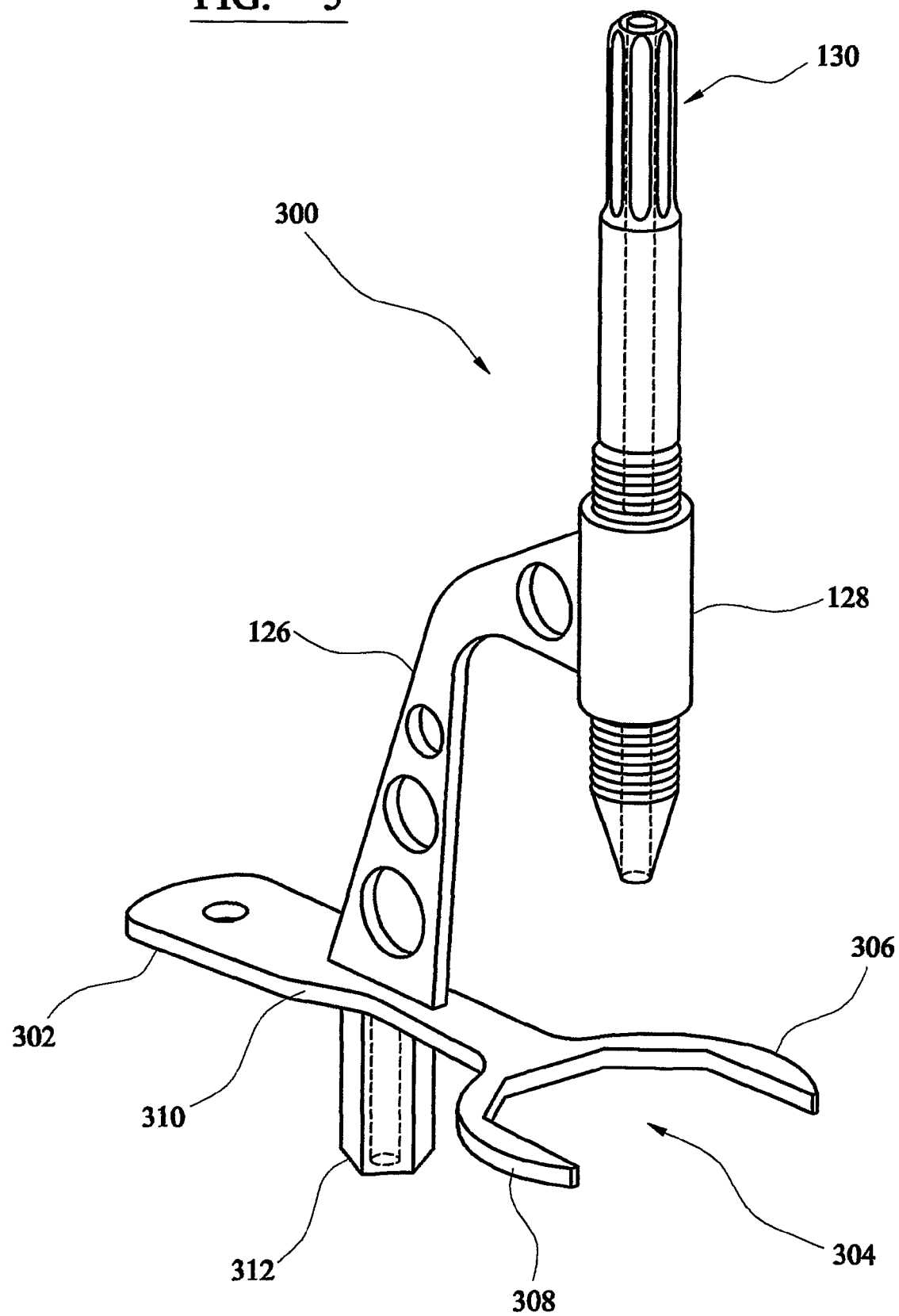
FIG. 5 shows a perspective view of a second surgical jig according to the present invention.

With reference to FIG. 5, there is shown a second surgical jig 300 according to the present invention. This jig is a simpler version of that shown in FIGS. 1 to 3 but has several parts in common. The jig 300 includes a handle 302 and a mouth 304 defined by jaws 306, 308 on opposing sides. An inner surface of mouth 304 has a shape adapted to engage with the anatomical features of a typical femoral neck. Support arm 126 extends from a body portion 310 of jig 300 and includes a guide 128 with instrument 130 located therein. Support arm 126 is slidably mounted on the body portion by a threaded stud (not shown) extending through a linear slot in body part 310 and extending along the central longitudinal axis of the jig. A straight channel is provided in the upper surface of body 310 in which the lower part of the arm is located and along which the arm can slide. A nut 312 is secured to the threaded stud, in order to retain the support 126 against body part 310.

Jaws 306 and 308 define a substantially flat plane and the central longitudinal axis of guide 128 extends in a direction substantially perpendicular to the plane of mouth 304.

Use of jig 300 is similar to that of jig 100 except that the separation of jaws 306 and 308 is not adjustable. Rather, in use, jig 300 is presented from the medial to lateral direction and the femoral neck is received within mouth 304. The nut 312 is slackened and the guide can be slid along the middle axis of the jig to more accurately determine axis of the femoral neck. The 312 nut is tightened and the Instrument 130 is rotated, using a tool if necessary, until the head of the instrument is brought into engagement with an upper surface of the femoral head with the jaws 306 and 308 engaging an under surface of the femoral head so as lock the jig in position. The spacing of the jaws 306, 308 helps to centralise the jig with respect to the medial to lateral axis of the femoral neck.

Figure 6:
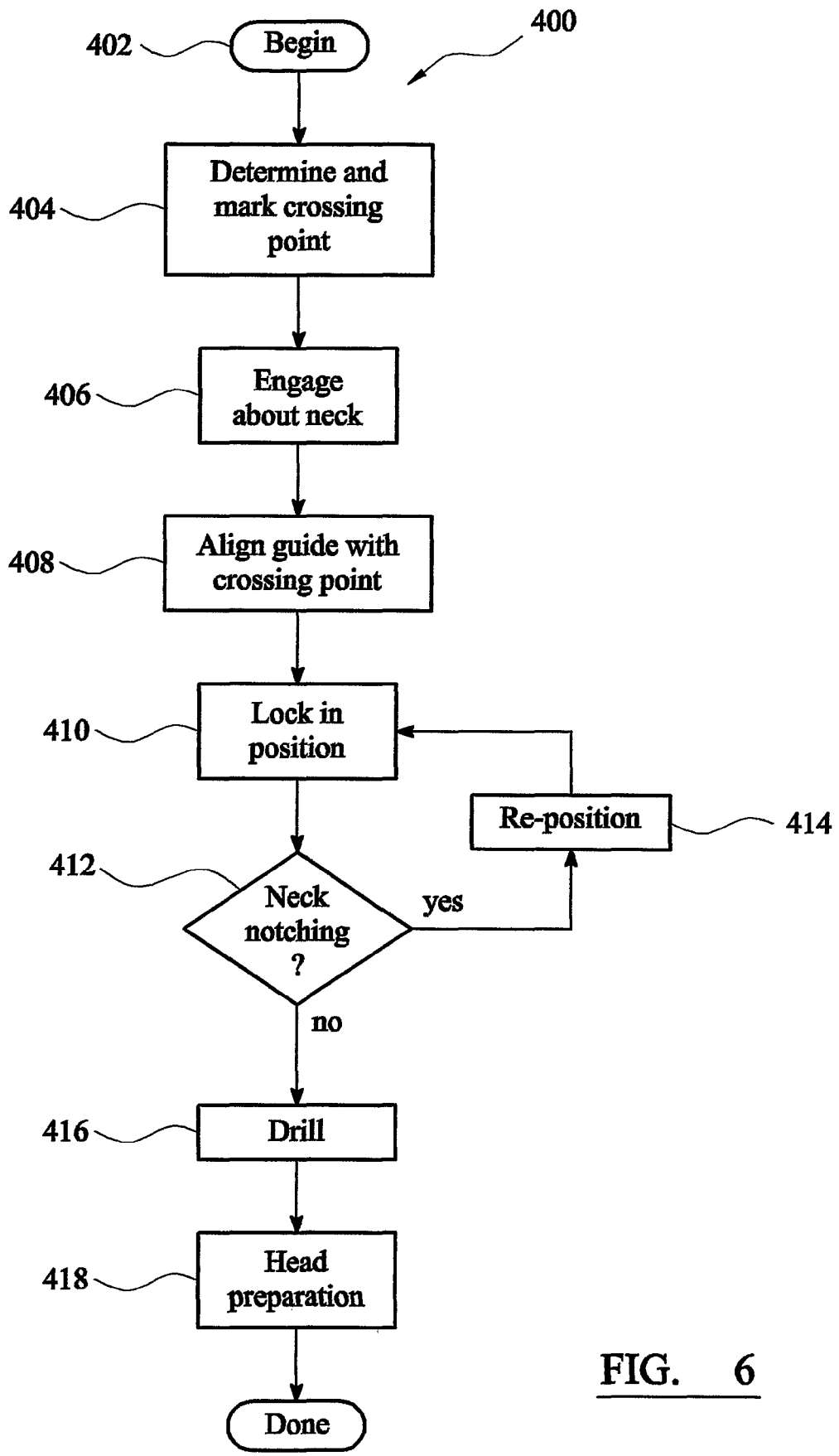
FIG. 6 shows a flow chart illustrating steps of a surgical procedure using a surgical jig according to a further aspect of the invention.

Use of the jig in a femoral head resurfacing surgical procedure will now be described in greater detail with reference to FIG. 6. FIG. 6 shows a flowchart 400 illustrating some of the steps carried out during a surgical procedure to resurface a femoral head. It will be appreciated that there are other surgical steps preceding and following the steps illustrated in FIG. 6 but these have not been described so as not to obscure the nature of the present invention.

After the surgical procedure has begun at step 402, at step 404, the surgeon visually locates the superior aspect lines and the posterior aspect line and determines where they cross on the femoral head. The crossing point is then marked to provide a visual aid. Wheel 168 is rotated to open the mouth of the jig, if necessary, and the mouth is presented in a medial to lateral direction to engage the neck at step 406. The wheel 168 is rotated in the opposite direction to close the jaws about the femoral neck with the concave formations 121, 122 being located about the anatomical features of the femoral neck. The jig can be manipulated by the surgeon until the surgeon is satisfied that the jig is correctly located about the femoral neck and then the wheel rotated further so as to tighten the jaws about the neck. At step 408, the support 120 can be slid along the forceps, until the central axis of guide 128 is located near the crossing point as previously identified by the surgeon. Once the axis of the guide is considered to coincide with the axis of the femoral neck, the jig can be locked in position at step 410 by rotating instrument 130, using a tool if necessary, until the head of the instrument engages against the femoral head upper surface thereby locking the jig in place.

An optional step of determining whether the axis as determined by this jig position would likely result in notching of the femoral neck during subsequent head preparation steps can be carried out at step 412. A guide arm having a cylindrical body which can be mounted over instrument 130 so as to be journaled about portion 140 is slid over the instrument from above. The guide arm includes a stylus extending downwardly toward the femoral head and is rotated about the guide axis to help check whether cutting of the femoral head would likely result in notching of the femoral neck. If it is determine at step 412 that notching of the neck would likely occur, then at step 414, the jig can be loosened and repositioned before being locked back in position at step 410 and the neck notching checking step 412 carried out until the surgeon is satisfied that the selected axis will likely not result in neck notching. When the surgeon is satisfied with the selected axis, then a drill is introduced through bore 136 of instrument 130, which provides a bushing for the drill bit, and a hole drilled into the femoral head. The drilled hole can be used in subsequent steps 418 of the preparation of the femoral head and implantation of the head surface implant.

The above described surgical procedure relies to a large extent on the experience and skill of the surgeon. These abilities can be augmented by image guided surgery systems and the jig of the present invention can be adapted for use in image guidance surgical procedures. FIG. 7 shows a schematic plan view of a 'star' 420 which can be attached to the jig in order to provide a jig adapted for image guided surgery. The star provides a marker which is detectable by an image guided surgery system in order to determine the location in space of the jig. The star includes three arms 421, 422, 423 each of which bears a sphere 424, 425, 426 each of which has a surface which reflects infrared radiation. The star also includes a clamp or other connector by which the star is attached to the jig. The star can be permanently or releasably attached to a part of the support structure 120 such as arm 126. All that is required is that the star is stationary with respect to the central axis of the guide 128.

The configuration of the star (i.e. the angular displacement of the arms and length of arms) provides a signature to identify the jig to an image guided surgery (IGS) system. The IGS system is programmed with the necessary data to identify the position and orientation of the central axis of the guide 128 with respect to the centre of the star so that when the IGS system recognises the star, the location and position of the central axis of the guide relative to the star can be determined by the IGS system.

An alternative way of adapting the jig for use with an IGS system is to use an instrument 130 with an IGS marker therein. FIG. 8A shows a first example embodiment of an IGS adapted instrument 430. The instrument 430 is a cannulated probe 432 having a bore 434 extending along its length and first 436 and second 438 spherical members disposed around the instrument and centred on the central, longitudinal axis of the instrument.

In use, instrument 430 is inserted in the channel of guide 128 and its longitudinal axis is co-linear with the central longitudinal axis of the guide. The IGS system determines the locations in space of the two spheres and determines the line passing through the centres of the spheres and thereby can determine the position and direction of the guide axis in space.

Another example of an instrument 440 for use in an IGS embodiment of the jig is shown in FIG. 8B. The instrument includes a handle part 442 and a probe part 444 having a tip 446 at a distal end. Spheres 448 and 450 are mounted on the handle 442 with their centres co-linear with the central longitudinal axis of probe 444. In use, probe 444 is inserted in the channel of guide 128 and, similarly to instrument 430, the IGS system determines the location and direction of the guide axis which is co-linear with the central longitudinal axis of probe 444.

Although these embodiment has been described using markers in the form of infrared reflecting spheres, other IGS markers can be used and other ways of marking the jig and/or instruments in order to adapt the jig and/or instruments for use in an IGS system are possible. For example a wire based, rather than wireless, IGS marker can be used. Also, sonic rather than electromagnetic radiation based wireless signalling can be used. Forms of electromagnetic radiation other than infrared light can be used, such as radiation in the visible part of the spectrum or other parts of the electromagnetic spectrum, e.g. radio or microwave.

Figure 9:
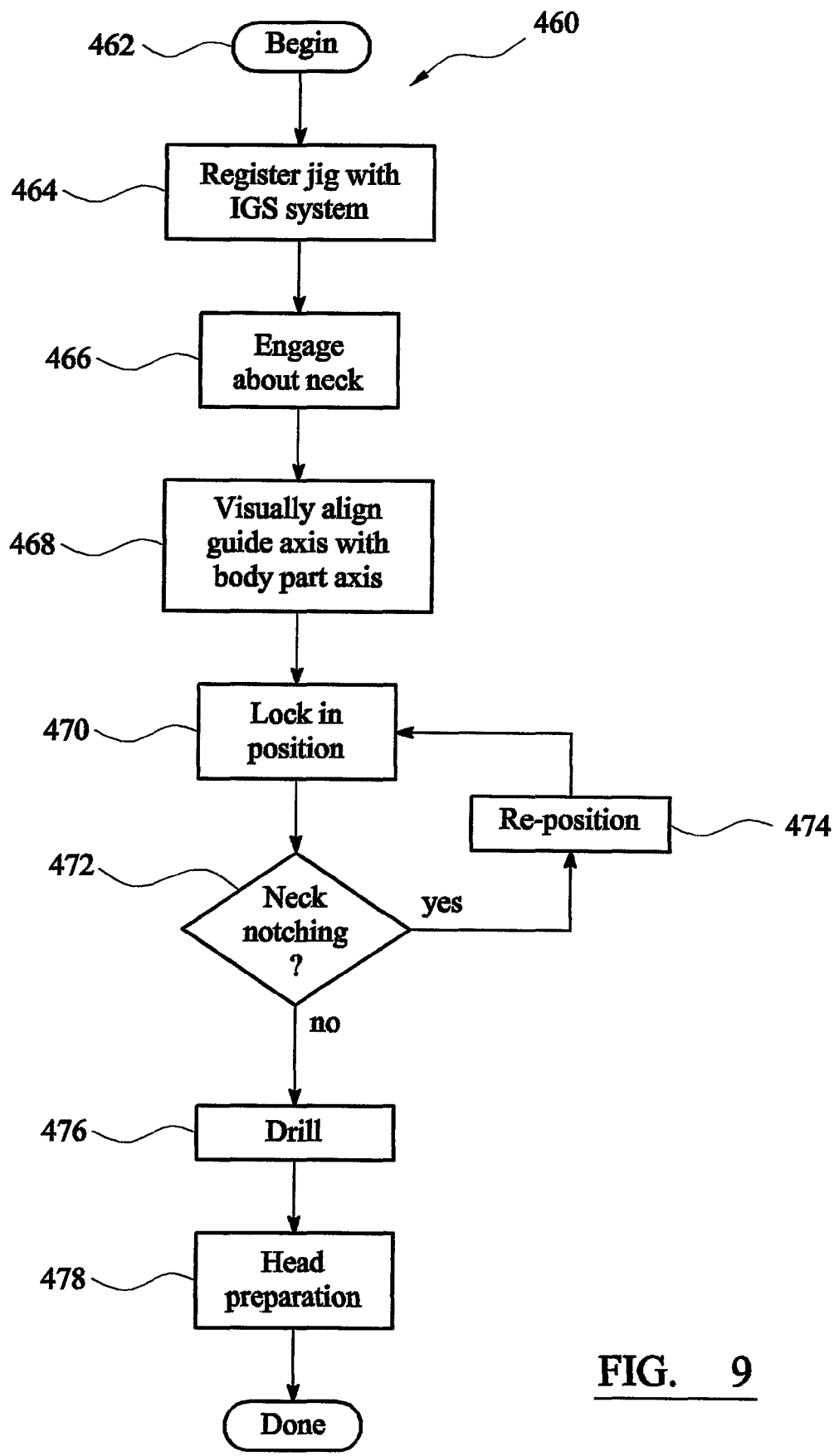
FIG. 9 shows a flow chart illustrating steps of a surgical procedure using an image guided surgery configured jig according to another aspect of the invention.

FIG. 9 shows a flowchart 460 similar to flowchart 400 illustrating some of the steps involved in an IGS surgical procedure for re-surfacing a femoral head. Again some of the preceding and following steps in the surgical procedure have been omitted for the sake of clarity. After the surgical procedure has begun at step 462, the jig is registered at step 466 with the IGS system. Owing to the configuration of the star mounted on the jig, once the jig has been identified to the system during a registration procedure, the IGS system can determine the position in space of the centre of the star and can compute therefrom the location and orientation in space of the axis of the guide relative to the position of the centre of the star. The forceps are opened, the mouth of the jig is presented to the neck and closed to engage the femoral neck at step 466.

The IGS system, based on previously obtained body data, such as from an X-ray, CT scan or similar, displays the axis of the body part with which it is desired to align the jig. For example, in a pre-operative procedure, the surgeon can have identified from body images and data the location of the femoral neck axis 406. At some stage in the procedure, IGS markers are placed on the body part and the body part is registered with the IGS system so that the IGS system can determine the location and orientation in space of the body part axis.

At step 468, the femoral axis as determined by the surgeon and determined by the IGS system from the body image data, is visually displayed together with the current position, in real time, of the axis of the guide 128 as determined by the IGS system. The surgeon then manipulates the jig at step 468, until the displayed central longitudinal axis of the guide 128 sufficiently closely corresponds with the displayed femoral neck axis. The instrument 130 is then screwed down until the head engages with the upper surface of the femoral neck so as to lock the jig in place at step 470. At steps 472 and 474, it can optionally be determined whether the currently determined axis would likely result in femoral neck notching during subsequent head preparation procedure steps and if so the jig can be repositioned. If the currently determined axis is acceptable, then a drill can be introduced through bore 136 of instrument 130 to create a hole in the head of the femur and into the femoral neck for use in subsequent head preparation steps 478.

FIG. 10A shows a body part 320 of a third surgical jig 320 according to the present invention. This jig is a further version of that shown in FIG. 5 and has several parts in common. The jig body is used with a jig arm the same as that shown in FIG. 5, but which is not shown in FIG. 10A for the purposes of clarity. Like Jig 300, the mouth of the jig has a central axis 322 substantially perpendicular to the plane defined by the mouth 304 of the jig. The five flat inner surfaces of the jaws of the mouth are each substantially tangential to a circle centred on the central axis 322. Hence the distance from the centre 322 to the first 324, second 326 and third 328 inner surfaces is the same.

The body of the jig 320, includes a narrow rectilinear trench 330. A plurality of equi-spaced apertures 332 are provided in the base of the trench. A graduated scale runs down the side of the trench. The scale includes indicia which indicates the degree of off-set from a circular femoral neck cross section. A zero off-set position is identified by a '0' indicia and other indicia indicate positive and negative off sets. In the illustrated embodiment, the positive off-sets are at 2 mm increments and are +2 mm, +4 mm and +6 mm. The negative off-sets are at 2 mm decrements and are −2 mm, −4 mm and −6 mm. It will be appreciated that different ranges of values can be used, different step sizes can be used, e.g. 1 mm step sizes, and values can be displayed in different units.

The trench 330 and apertures 332 are dimension and configured so that the threaded pin extending from the lower end of arm 126 can be received in a one of the apertures 332 and the lower end of the arm can be received in trench 330 so as to be constrained to slide along the trench in a longitudinal direction. Hence, the support arm 126 can be slid along the central longitudinal axis of the jig, and secured at discrete positions, so that the central axis of the guide bore can be located at fixed positions along the longitudinal, central axis of the jig, which includes axis 322. Knurled, threaded nut 312 can be used to secure the support arm to jig body 320 by being screwed onto the free end of the support arm pin passing through a one of the apertures 322.

Also shown in FIG. 10A is a schematic representation of a cross section 340 through a femoral neck. The cross sectional shape of the femoral neck can have an approximately oval or elliptical shape rather than a circular shape. Hence, in practice, the femoral neck can have a major axis 342 and a minor axis 344. The present invention is not limited to use on necks having such geometries as there can be a great variation in the actual cross sectional shape of a femoral neck. For example, some necks can have a generally triangular cross sectional shape. Hence the femoral neck cross sectional shape shown in FIG. 10A is merely so as to illustrate the general concept of locating the central femoral neck axis 346 while taking into account the effect of any non-circular symmetries.

Figure 11:
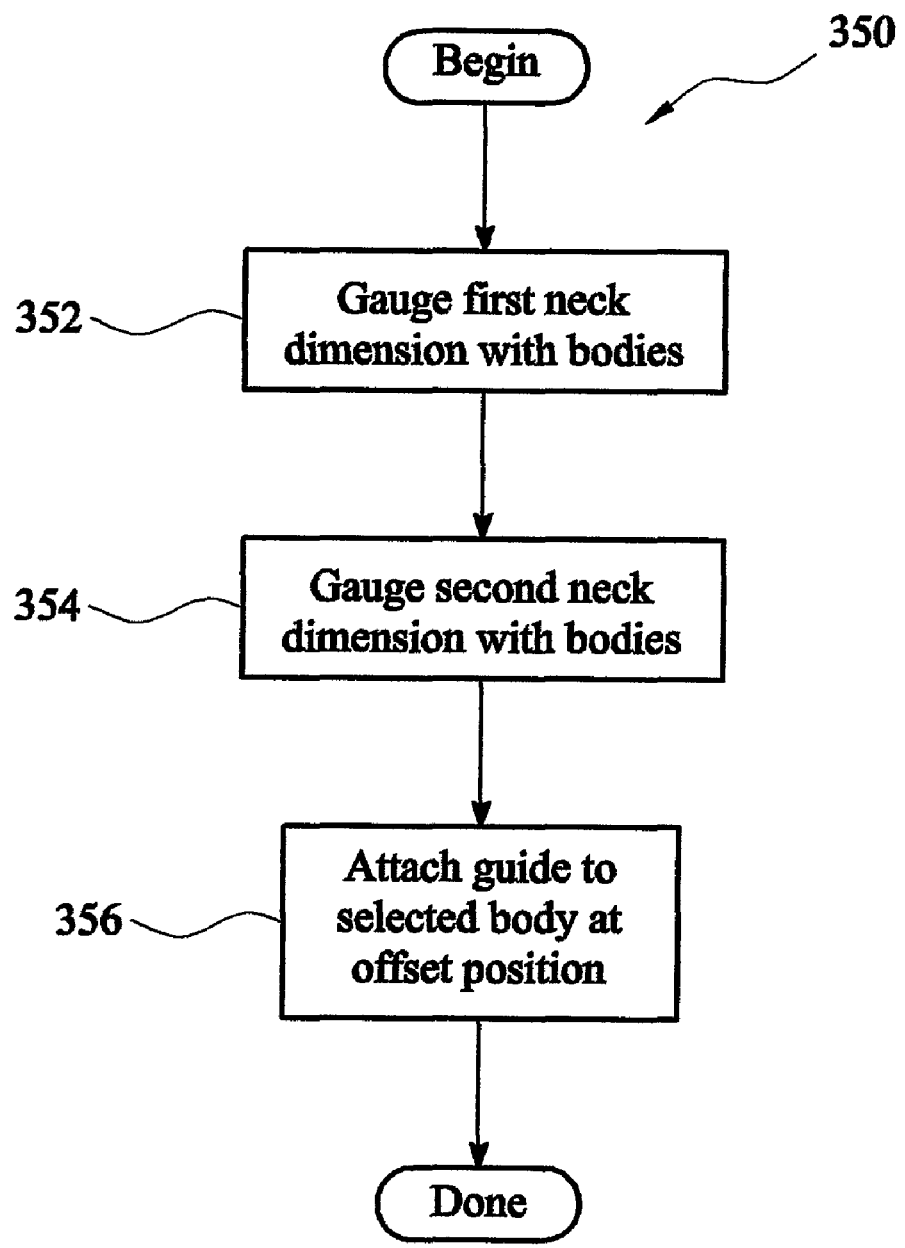
FIG. 11 shows a flow chart illustrating a method of using the jig illustrated in FIGS. 10A and 10B according to the invention.

A method 350 of using a jig, or series of jigs, similar to that shown in FIG. 10A will now be described with reference to FIG. 11. The surgeon is provided with a series of jigs 320 each having a slightly different mouth width, or diameter. For example, a series of jigs having mouth widths in the range of 40 mm, 42 mm, 44 mm, 46 mm, 48 mm and 50 mm can be provided. At step 352, the surgeon uses the jig bodies, without the support arm attached, to gauge the size of the femoral neck in a first dimension, by engaging the femoral neck within the mouth 304 of the jig body. For example, through a combination of feel and manipulation, the surgeon may determine that the longer dimension of the neck 342 is approximately 46 mm. Then at step 354, the surgeon uses the jig bodies, without the support arm attached, to gauge the size of the femoral neck in a second dimension, by engaging the femoral neck within the mouth 304 of the jig body. The second dimension may be generally perpendicular to the first dimension but need not be and will depend on the geometry of any particular neck. For example, through a combination of feel and manipulation, the surgeon may determine that the shorter dimension 346 of the neck is approximately 40 mm.

Hence, the actual centre of the femoral neck will be off set from the centre 322 of the mouth of the jig by approximately one half of the difference between the longer and shorter dimensions: in this case approximately 3 mm. The surgeon can then select either the 46 mm mouth diameter jig handle or the 40 mm diameter mouth jig handle, depending on accessibility at the surgical site. At step 356, the surgeon attaches the support arm 126 to the jig body at the correct, or approximately correct, off-set position.

If the larger diameter is being used, then the guide axis is off set by approximately −3 mm, as the femoral neck will enter 3 mm further into the mouth of the jig than a circularly symmetric neck would. Therefore the surgeon, can select to attached and fasten the support arm 126 with the pin in the aperture corresponding to either the −2 mm indicium or −4 mm indicium on the scale 334. As the end of the support arm is snugly located within trench 330, rotation of arm 126 is prevented and the central axis of the guide bore is constrained to fall on the longitudinal axis of the jig body, at position 336. Hence, the surgeon can then 'blindly' engage the jig about the femoral head, and can use feel alone to determine when the jig is in the correct position as the jig has been pre-calibrated to the femoral neck geometry. Therefore the surgeon does not need to change the location of the support arm along the longitudinal axis of the jig body. This increases the ease of use of the jig, especially when access to, or visibility at, the surgical site is restricted. The further use of the jig by the surgeon can then be generally similar to the methods described above.

If the smaller jig mouth diameter, 40 mm, is being used, then the guide axis is off set by approximately +3 mm, as the femoral neck axis will extend 3 mm further out of the mouth of the jig than a circularly symmetric neck would. Therefore the surgeon, can select to attached and fasten the support arm 126 to the 40 mm mouth diameter jig with the pin in the aperture corresponding to either the +2 mm indicium or +4 mm indicium on the scale 334. The assembled jig is then used as described above.

FIG. 10B shows an embodiment of a further jig body 360 similar to jig body 320. However, in this embodiment, instead of having a plurality of separate apertures 332, a single elongate aperture 362 is provided so as to provide a continuous range of off set positions. A graduated scale 364 is also provided together with an indicium 366 indicating the zero off set position. An indicium or marking can be provided toward the base part of the support arm 126, so positioned that when aligned with the zero off set indicium, the bore axis of the guide is co-linear with the central axis 322 of the mouth. For this illustrated embodiment of the jig body, the threaded pin of the support arm can have a generally circular cross section, but with flattened portions on opposed sides which slidingly engaged within slot 362 so as to prevent rotation of the support arm. In another embodiment, jig body 360 can include a trench, similar to trench 330, having slot aperture 362 running along the bottom of the trench. The interaction between the trench and the base part of the support arm constrains the support arm to linear motion and prevents rotation. It will be appreciated that the slot provides a finer degree of tuning of the off set position of the guide bore axis as any of a range of positive and negative off sets can be provided, e.g. approximately 3 mm for the above described example. The indicium on the base of the support arm can be aligned with a one of the graduation marks of the scale 364, which can include indicia representing the quantitative amount of the off set, so as to attach and fix the support arm with the appropriate off set for the femoral neck geometry.

It will be appreciated that various modifications and changes can be made to the specific embodiments described above and also that some of the steps illustrated in the flowcharts may be optional and/or their sequence may be changed. Therefore the above description is by way of example only and various modifications and changes are envisaged.

The invention claimed is:

1. A surgical jig for use in determining an axis relative to a body part, the jig comprising:
    a handle having a first arm and a second arm pivotally connected to one another, each of which have a proximal end and a distal end, the distal ends of the first arm and the second arm defining a substantially flat plane and forming a mouth having a middle axis for engaging the body part;
    a guide having a channel with a guide axis substantially perpendicular to the plane;
    a support attaching the guide to the handle, wherein the guide is translatable relative to the mouth in a plane parallel to the substantially flat plane while maintaining the guide axis substantially perpendicular to the plane;
    a first threaded boss located on the first arm and a second threaded boss located on the second arm; and
    a threaded shaft extending between the bosses perpendicular to the middle axis, the shaft having opposite sense screw threads on either end, wherein rotation of the shaft in a first direction moves the distal ends of the first arm and the second arm away from one another, and rotation of the shaft in a second direction moves the distal ends of the first arm and the second arm toward one another.

2. The jig of claim 1, wherein the mouth includes formations adapted to mate with an anatomical feature of the body part.

3. The jig of claim 2, wherein the formations comprise a first concave formation and a second concave formation located on opposite sides of the mouth and oriented in opposition to each other.

4. The jig of claim 1, wherein the support provides a sight.

5. The jig of claim 1, wherein the support is constrained to translate along the middle axis.

6. The jig of claim 1, wherein the support slidingly engages with the handle.

7. The jig of claim 1, wherein the support comprises an arm having a first end and a second end, the guide being attached at the first end and the support being mounted to the handle by the second end.

8. The jig of claim 1, wherein the first and second arms form a forceps.

9. The jig of claim 1, wherein the threaded shaft extends perpendicular to the guide axis.

10. The jig of claim 1, further comprising a lock operable to lock the first arm and the second arm with respect to one another.

11. The jig of claim 1, wherein the support further comprises a base attached to the second end of the arm.

12. The jig of claim 11, wherein the base is constrained to slide along the middle axis.

13. The jig of claim 12, wherein the first arm and the second arm are pivotally connected at their distal ends by a pivot, and the base has a retaining formation located along the middle axis, and wherein the base co-operates with the pivot and retaining formation so as to be constrained to slide along the middle axis.

14. The jig of claim 1, further comprising a drive wheel mounted on the threaded shaft for rotating the shaft.

15. The jig of claim 14, wherein the drive wheel provides the retaining formation.

16. The jig of claim 1, further comprising marker detectable by an image guided surgery system to locate the jig.

17. The jig of claim 16, wherein the marker is stationary relative to the guide.

18. The jig of claim 16, wherein the marker is wirelessly detectable.

19. The jig of claim 1, the jig further comprising an instrument with at least a straight portion within the channel and extending at least partially along the axis.

20. The jig of claim 19, wherein the instrument is cannulated.

21. The jig of claim 19 wherein the instrument is a drill guide.

22. The jig of claim 19, wherein the instrument is movable along the guide axis.

23. The jig of claim 19, wherein the instrument is resiliently biased toward the mouth.

24. The jig of claim 19, wherein the instrument and the guide provide between them an external thread and an internal thread.

25. The jig of claim 19, wherein the instrument includes a portion having a smooth outer surface and a right circular cylindrical shape, providing an axle about which a part of a checking stylus can be journaled for rotation about the axis.

26. The jig of claim 19, wherein the instrument includes a marker detectable by an image guided surgery system to locate the axis.

* * * * *